United States Patent [19]

Shroot et al.

[11] 4,405,615
[45] Sep. 20, 1983

[54] COMPOSITION FOR TREATMENT OF PSORIASIS CONTAINING 10-SUBSTITUTED 1,8-DIHYDROXY-9-ANTHRONES

[75] Inventors: Braham Shroot, Antibes; Jean Maignan, Tremblay les Gonesse; Gerard Lang, Epinay-sur-Seine, all of France

[73] Assignee: Groupement d'Interet Economic dit: Centre International de Recherches Dermatologiques C.I.R.D., Valbonne, France

[21] Appl. No.: 330,472

[22] Filed: Dec. 14, 1981

[30] Foreign Application Priority Data

Dec. 15, 1980 [FR] France .................. 80 26550

[51] Int. Cl.³ .................................. A61K 31/625
[52] U.S. Cl. ........................ 424/232; 424/234; 424/240; 424/285; 424/308; 424/317
[58] Field of Search ............ 424/232, 234, 317, 285, 424/308; 549/253; 562/460, 461; 560/52

[56] References Cited

U.S. PATENT DOCUMENTS 3,835,167 9/1974 Pfister .................... 260/351
3,923,838 12/1975 Eilingsfeld et al. ........... 260/346.3

OTHER PUBLICATIONS

Schultz et al.–Chemical Abstracts 88:104984g and 88:104985h (1978).

*Primary Examiner*—Leonard Schenkman
*Attorney, Agent, or Firm*—Wegner & Bretschneider

[57] ABSTRACT

A method for the treatment of psoriasis uses a composition which contains in an appopriate vehicle for topical application at least one active ingredient corresponding to the formula:

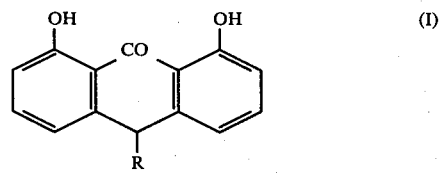

wherein R is a radical of the group represented by

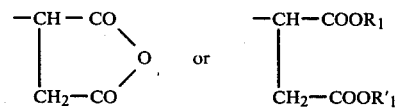

wherein $R_1$ and $R'_1$ are identical or different and represent H, methyl or ethyl.

21 Claims, No Drawings

COMPOSITION FOR TREATMENT OF PSORIASIS CONTAINING 10-SUBSTITUTED 1,8-DIHYDROXY-9-ANTHRONES

The present invention relates to new compositions for the treatment of psoriasis which are applied to the skin containing 10-substituted 1,8-dihydroxy-9-anthrone and to a process for the treatment of psoriasis. Preferred 10-substituted 1,8-dihydroxy-9-anthrones are the diacid in which the 10-substituent is of the formula —CH(COOH)—CH₂—COOH, the methyl and the ethyl esters and the anhydride thereof.

Psoriasis is a particularly frequent dermatosis which may affect 2 to 3% of the population and represents 4 to 5% of the dematological conditions at this time.

Psoriasis manifests itself by the presence of erythematosquamous plaques which are rather limited. Histological examination shows a considerable thickening of the epidermis with focuses of polynuclear microabcesses which produce a pustular dermatosis.

Generally, the lesions produced by psoriasis are found in joints, on the posterior surface of the forearms, the knees, the legs, and in the sacro-lumbar regions. Psoriasis also manifests itself on hairy skin and the nails.

Treatment of psoriasis is particularly difficult in view of the different forms which it may take. It may consist of local or systemic treatment. In the case of local treatment, it is necessary to produce a cleansing of the squamous lesions followed by treatment of the erythematous plaques by local corticotherapy or by classic reduction, such as with ichtyol, tar, chrysarobin and its derivatives, or cade oil.

Systemic treatments are rather numerous and one can cite particularly vitamin therapy, especially the use of vitamin A, placental extracts, liver factors, sedatives, and synthetic antihistamines.

Among the treatments recently proposed are the utilization by topical route or by injection of a combination of cycloheximide or a derivative of cycloheximide with an anti-inflammatory glucocorticoid steroid.

Although these various treatments permit in certain cases an initial remission of symptoms, each of these treatments presents certain inconveniences, for instance a temporary and incomplete attenuation of the symptoms, a rapid reappearance of the psoriasis when the attenuation has ended, a serious alteration and sometimes an atrophy resulting from the topical application of glucocorticoids for prolonged periods.

According to the invention, one considers psoriasis attenuated when a psoriatic lesion is significantly reduced in thickness or notably but not completely removed or totally removed.

It has been noted, that by use of the present invention, psoriasis could be attenuated by treating the affected regions with the aid of a composition containing in an appropriate vehicle for topical application at least one compound of the formula

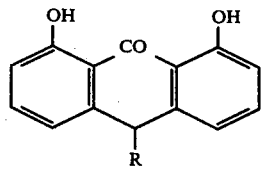

wherein R is a radical of the group represented by

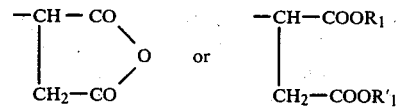

wherein $R_1$ and $R'_1$ are identical or different and represent H, methyl or ethyl or one of the isomers thereof.

Among the compounds of formula (I), which may be used in the compositions according to the invention for the treatment of psoriasis, are:
- 10-(1,8-dihydroxy-9-anthron)ylsuccinic anhydride,
- 10-(1,8-dihydroxy-9-anthron)ylsuccinic acid,
- 10-(1,8-dihydroxy-9-anthron)ylsuccinic acid dimethyl ester,
- 10-(1,8-dihydroxy-9-anthron)succinic acid diethyl ester,
- methyl 3-carboxy-3[10-(1,8-dihydroxy-9-anthron)yl]-propionate, and
- ethyl 3-carboxy-3-[10-(1,8-dihydroxy-9-anthron)yl]-propionate.

Topical application according to the invention can employ utilization of an active compound incorporated in a base or a pharmaceutical vehicle convenient for application on the place of the lesion so that a local effect can be produced. These compositions for topical administration can be, for example, solutions, lotions, suspensions, pastes, ointments, gels, aerosol compositions, etc.

The term ointment covers formulations, such as creams containing absorbable oil bases of the water soluble type or of the emulsion type, for example petrolatum, lanolin, polyethylene glycols, as well as mixtures thereof.

These ointments can be prepared by dispersion of the active principle in convenient bases such as petrolatum, lanolin, polyethylene glycols, and their mixtures. It is preferable that the active compound be finely divided by means of a colloid mill using for example light liquid petrolatum as levigating agent before dispersion in the ointment base. Creams which are of the oil-in-water or water-in-oil type are prepared by dispersing the active compound in the oily phase before preparing an emulsion of that phase with the aqueous phase.

The compositions according to this invention generally contain 0.05 to 5% and preferably 0.1 to 3% by weight of the active principle of formula (I) relative to the total weight of the composition.

The compositions according to the invention may also contain additional active principles such as salicylic acid, hydrocortisone, etc.

The treatment of psoriasis consists of applying to the lesions, after they have been cleaned, a sufficient quantity of a composition according to the invention and protecting the place thus treated, advantageously by utilization of a protective bandage.

The treatment may be accompanied by ultraviolet radiation using repeated exposure and adopting a schedule of decreasing weekly exposures until the various lesions are attenuated or have totally disappeared.

The active compounds used in the compositions according to this invention are mostly known and are prepared by the Michael reaction in which 1,8-dihydroxy-9-anthrone (anthralin) is reacted in an inert atmosphere in an organic solvent, such as dimethylformamide, chloroform, or acetonitrile, optionally in the presence of a basic catalyst, with an unsaturated compound in which the double bond is conjugated and activated by an unsaturated electronegative group.

The reaction is generally conducted at the boiling temperature of the organic solvent and one utilizes preferably as a basic catalyst dimethylamino-4-pyridine or sodium methylate.

When the product crystallizes from the reaction mixture in the course of its formation or on cooling, it is separated by filtration, washed and dried under reduced pressure.

In other cases the reaction mixture is concentrated under reduced pressure and the residue is either crystallized in an appropriate solvent or purified by chromotography on silica gel.

The following examples which are given for purposes of illustration and not to limit the invention in scope. They show the preparation of the active compounds as well as several examples of compositions which can be used for topical application in treatment of psoriasis.

EXAMPLE I

Preparation of 10-(1,8-dihydroxy-9-anthron)ylsuccinic anhydride

A mixture of 28.6 g of anthralin (0.13 mol), 15 g of recrystallized maleic anhydride (0.15 mol) in 250 ml of dimethylformamide is placed in an inert atmosphere protected against air humidity and against light and is maintained for an hour at a temperature of 120° C. The reaction mixture is filtered at that temperature. To the filtrate, brought to ordinary temperature, one adds several ml of water until the product begins to crystallize. After several hours the solid is suction dried, and analysed. One isolates thus 26 g of 10-(1,8-dihydroxy-9-anthron)ylsuccinic anhydride of yellow color decomposing at 260° C.

Analysis: $C_{18}H_{12}O_6$; Calc. C: 66.57, H: 3.73, O: 29.60; Found 66.53, 3.82, 229.54.

According to O. Schultz and G. Frey, Arch. Pharm. 310, pages 776–780 (1977), this compound has a melting point with decomposition of 230°–253° C.

EXAMPLE II

Preparation of 10-(1,8-dihydroxy-9-anthron)ylsuccinic acid

The anhydride prepared in Example I (10 g) is dissolved in a mixture of 350 ml of acetic acid and water (1:1) at 100° C. and the resulting solution is filtered while hot. The filtrate is permitted to stand at room temperature with exclusion of light. The crystalline diacid is suction filtered and then dried. One thus obtains 10 g of bright yellow crystals of a melting point of about 237° C.

Analysis: $C_{18}H_{14}O_7$; Calc. C: 63.16, H: 4.12, O: 32.72; Found 63.24, 4.16, 32.91.

According to O. Schultz and G. Frey (loc. cit.) this compound has a melting point of 232°–233° C.

EXAMPLE III

Preparation of 10-(1,8-dihydroxy-9-anthron)ylsuccinic acid dimethyl ester

To a solution of 6.78 g of anthralin (0.03 mol) and an excess of dimethyl maleate (0.06 mol) in 50 ml of chloroform placed in an inert atmosphere with exclusion of air humidity and light, one adds 0.5 ml of a 1% solution of sodium methylate. The reaction mixture is then kept at the boiling point for two hours. After cooling, it is applied directly on a silica gel chromotography column.

The product obtained is eluted by chloroform. The chloroform phases are concentrated. The crystallized diester is collected on a filter and dried. One obtains thus 10 g of pale yellow crystals with a melting point of 137° C.

Analysis: $C_{20}H_{18}O_7$; Calc. C: 64.86, H: 4.90, O: 30.24; Found 64.72, 4.92, 30.05.

EXAMPLE IV

Preparation of methyl 3-carboxy-3-[10-(1,8-dihydroxy-9-anthron)yl]propionate

A mixture of 7 g of anthralin (0.031 mol) and 4.42 g of methyl monomaleate (0.034 mol) in 100 ml of acetonitrile is brought to the boiling point for two hours in an inert atmosphere under exclusion of light and humidity, at which time all of the anthralin is transformed. The solvent is then evaporated under reduced pressure.

The solid obtained is washed with a mixture of water and acetic acid and then dissolved in methanol. The solution is filtered and then concentrated. The yellow crystals obtained (10 g) are dried. They start to decompose beginning at 168° C.

Analysis: $C_{19}H_{16}O_7$; Calc. C: 64.04, H: 4.52, O: 31.43; Found 63.88, 4.53, 31.36.

EXAMPLE V

Ointments are prepared according to the invention for application on the lesions starting with the following ingredients:

EXAMPLE A

| | |
|---|---|
| 10-(1,8-dihydroxy-9-anthron)ylsuccinic acid | 2 g |
| Petrolatum U.S.P. | 98 g |

EXAMPLE B

| | |
|---|---|
| 10-(1,8-dihydroxy-9-anthron)ylsuccinic acid | 2 g |
| Hydrocortisone | 1 g |
| Petrolatum U.S.P. | 97 g |

EXAMPLE C

| | |
|---|---|
| methyl 3-carboxy-3-[10-(1,8-dihydroxy-9-anthron)yl]propionate | 2 g |
| salicylic acid | 2 g |
| Petrolatum U.S.P. | 96 g |

EXAMPLE D

| | |
|---|---|
| ethyl 3-carboxy-3-[10-(1,8-dihydroxy-9-anthron)yl]propionate | 2 g |
| Hydrocortisone | 1 g |
| Petrolatum U.S.P. | 97 g |

EXAMPLE E

| | |
|---|---|
| 10-(1,8-dihydroxy-9-anthron)ylsuccinic anhydride | 0.5 g |
| salicylic acid | 2 g |
| Petrolatum U.S.P. | 97.5 g |

EXAMPLE F

| | |
|---|---|
| 10-(1,8-dihydroxy-9-anthron)ylsuccinic acid dimethyl ester | 3 g |
| salicylic acid | 2 g |
| Petrolatum U.S.P. | 95 g |

EXAMPLE G

| | |
|---|---|
| 10-(1,8-dihydroxy-9-anthron)ylsucccinic acid | 1 g |
| Solid paraffin | 5 g |
| Starch | 50 g |
| Soft white paraffin | 44 g |

What is claimed is:

1. A method of treating a patient suffering from psoriasis which comprises topically administering to the skin of said patient in a suitable vehicle a dose effective for the attenuation of psoriasis of at least one compound of the formula:

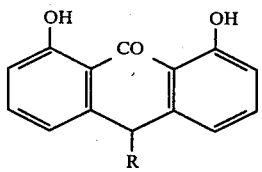

wherein R is

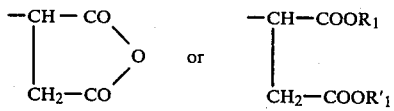

wherein $R_1$ and $R'_1$ are identical or different and represent H, methyl or ethyl.

2. A method of claim 1, wherein said compound is 10-(1,8-dihydroxy-9-anthron)ylsuccinic anhydride.
3. A method of claim 1, wherein said compound is 10-(1,8-dihydroxy-9-anthron)ylsuccinic acid.
4. A method of claim 1, wherein said compound is 10-(1,8-dihydroxy-9-anthron)ylsuccinic acid dimethyl ester.
5. A method of claim 1, wherein said compound is 10-(1,8-dihydroxy-9-anthron)ylsuccinic acid diethyl ester.
6. A method of claim 1, wherein said compound is methyl 3-carboxy-3-[10-(1,8-dihydroxy-9-anthron)yl]propionate.
7. A method of claim 1, wherein said compound is ethyl 3-carboxy-3-[10-(1,8-dihydroxy-9-anthron)yl]propionate.
8. A method of claim 1 wherein said vehicle is a solution, lotion, suspension, paste, ointment, gel, or aerosol.
9. A method of claim 1 or 8 wherein said compound is present in an amount of 0.05 to 5% on the basis of the total weight of the composition.
10. A method of claim 1 or 8 wherein said compound is present in an amount of 0.1 to 3% on the basis of the total weight of the composition.
11. A method of claim 1 or 8 wherein said vehicle includes salicylic acid or hydrocortisone.
12. A composition for topical treatment of psoriasis by application to the skin, containing in a pharmaceutically acceptable lotion, suspension, paste, ointment, gel or aerosol vehicle an amount of at least one active ingredient effective for treatment of psoriasis of the formula:

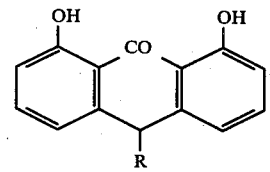

wherein R is

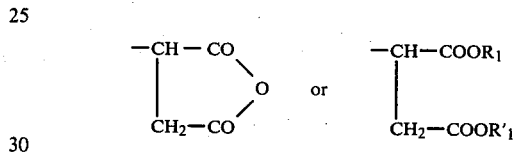

wherein $R_1$ and $R'_1$ are identical or different and represent H, methyl or ethyl.

13. A composition according to claim 12, wherein said active ingredient is 10-(1,8-dihydroxy-9-anthron)ylsuccinic anhydride.
14. A composition according to claim 12, wherein said active ingredient is 10-(1,8-dihydroxy-9-anthron)ylsuccinic acid.
15. A composition according to claim 12, wherein said active ingredient is 10-(1,8-dihydroxy-9-anthron)ylsuccinic acid dimethyl ester.
16. A composition according to claim 12, wherein said active ingredient is 10-(1,8-dihydroxy-9-anthron)ylsuccinic acid diethyl ester.
17. A composition according to claim 12, wherein said active ingredient is methyl 3-carboxy-3-[10-(1,8-dihydroxy-9-anthron)yl]propionate.
18. A composition according to claim 12, wherein said active ingredient is ethyl 3-carboxy-3-[10-(1,8-dihydroxy-9-anthron)yl]propionate.
19. A composition of claim 12 wherein said active ingredient is present in an amount of 0.05 to 5% on the basis of the total weight of the composition.
20. A composition of claim 12 wherein said active ingredient is present in an amount of 0.1 to 3% on the basis of the total weight of the composition.
21. A composition of claim 12 which includes salicylic acid or hydrocortisone.

* * * * *